United States Patent [19]

Shoher et al.

[11] Patent Number: 5,074,791
[45] Date of Patent: * Dec. 24, 1991

[54] METHOD FOR CONSTRUCTING A DENTAL BRIDGE USING A PREFABRICATED PONTIC

[76] Inventors: Itzhak Shoher, 50 Shlomo-Hamelech St., Tel-Aviv, Israel, 64386; Aharon E. Whiteman, 13 J. L. Perez St., Petach-Tikvah, Italy, 49206

[*] Notice: The portion of the term of this patent subsequent to Mar. 5, 2008 has been disclaimed.

[21] Appl. No.: 552,866

[22] Filed: Jul. 16, 1990

Related U.S. Application Data

[63] Continuation-in-part of Ser. No. 97,824, Sep. 17, 1987, Pat. No. 4,957,439.

[51] Int. Cl.$^5$ .............................................. A61C 13/12
[52] U.S. Cl. .................................. 433/180; 433/181; 29/160.6
[58] Field of Search ............... 433/180, 181, 182, 183, 433/9, 218, 223; 29/160.6

[56] References Cited

U.S. PATENT DOCUMENTS 4,704,089 11/1987 Shoher et al. ..................... 433/183
4,957,439 9/1990 Shoher et al. ..................... 433/180

Primary Examiner—Gene Mancene
Assistant Examiner—Adriene B. Lepiane

[57] ABSTRACT

A method for constructing a dental bridge using a prefabricated pontic, comprising positioning the pontic between metal retainers placed on a die formed from an impression of the abutment teeth to be restored, with the pontic having an arm with a free end extending approximate each metal retainer. The pontic and metal retainers are invested with refractory investment for forming a soldering model. A dental material composed of high- and low-fusing temperature metal particles form a porous structure defining an interproximal joint between the free end of each pontic and the corresponding retainer. A dental solder is added over the dental material and the model is heat treated to a first temperature above the melting temperature of the low-fusing temperature metal particles in the dental material. The temperature is then raised to melt the dental solder which fills the voids in the porous structure to form a solid joint between the pontic and each retainer of superior strength.

7 Claims, 2 Drawing Sheets

FIG. 1
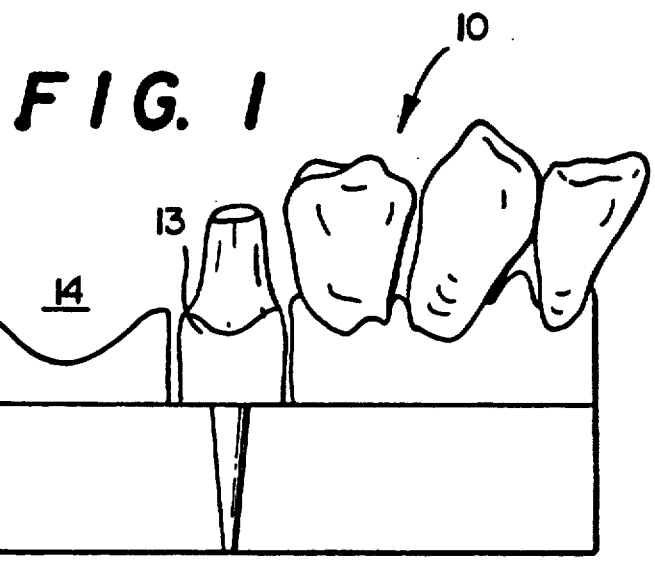
FIG. 2
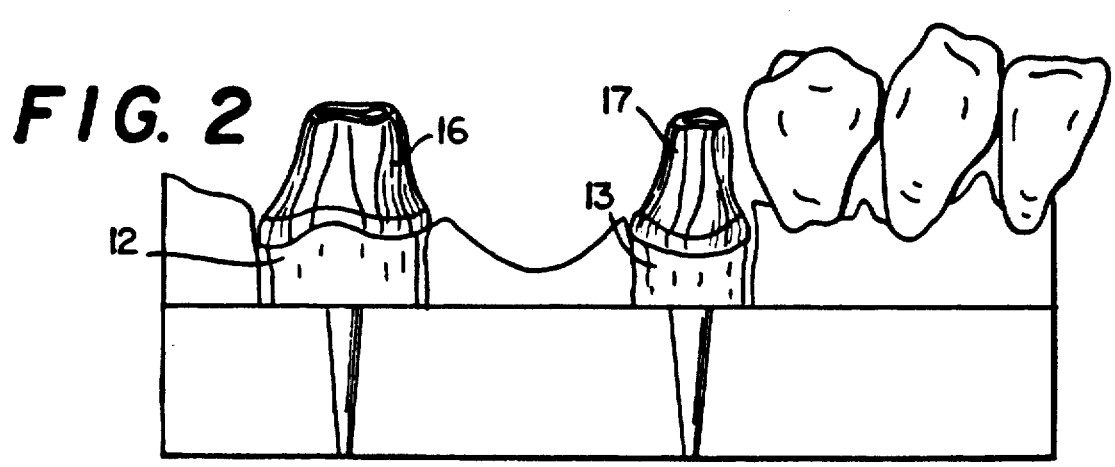
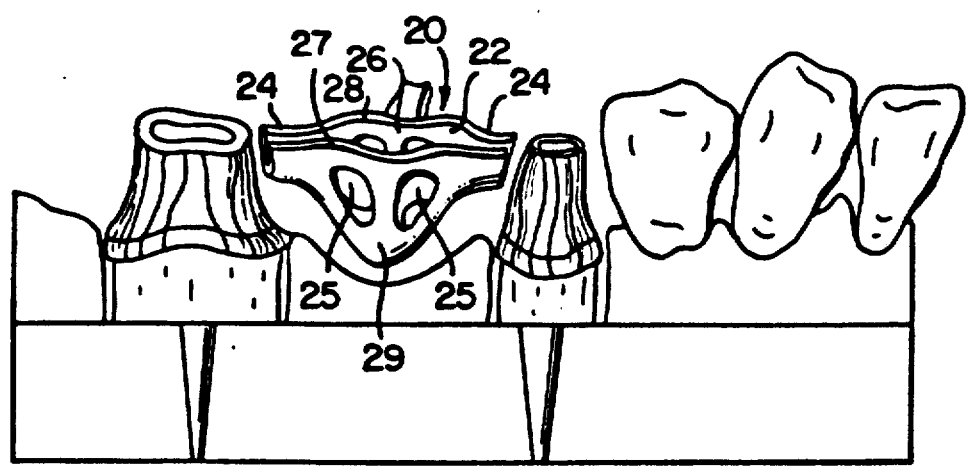
FIG. 3

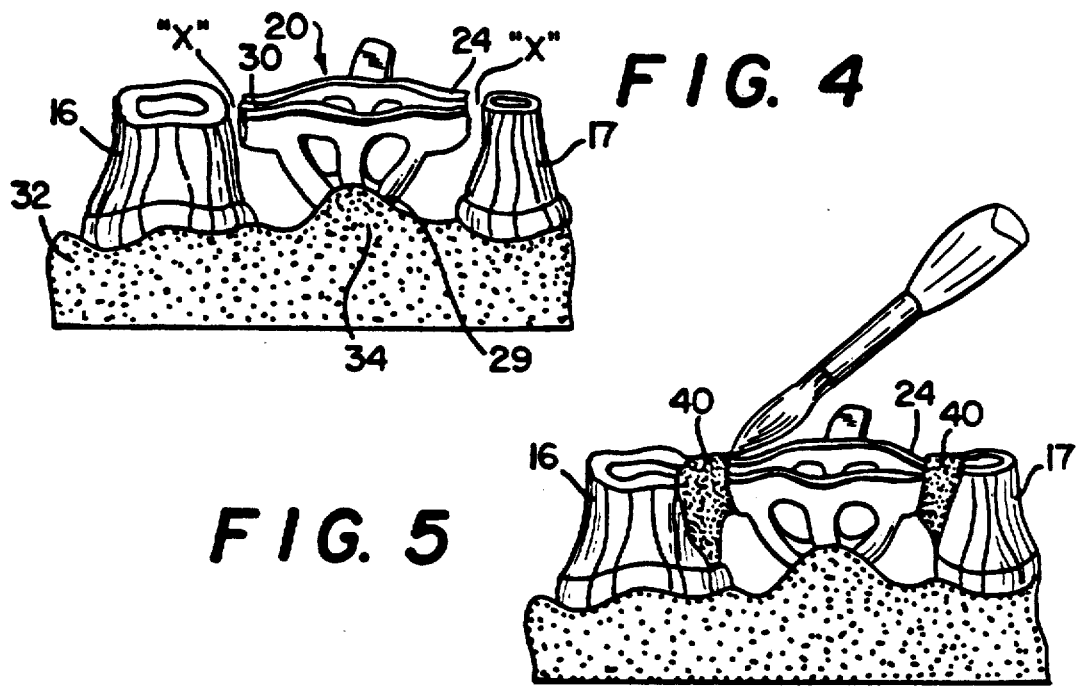
FIG. 4
FIG. 5
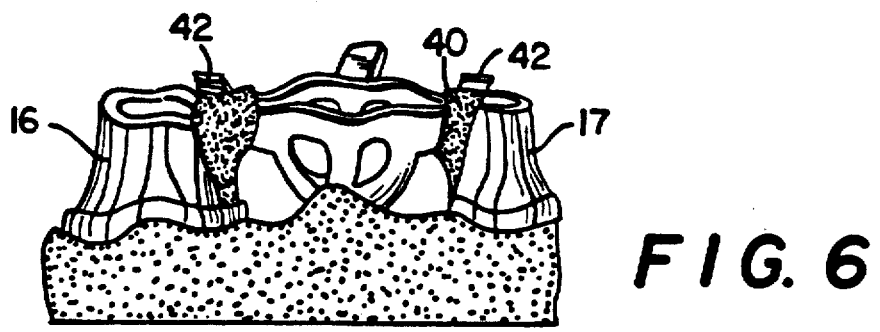
FIG. 6
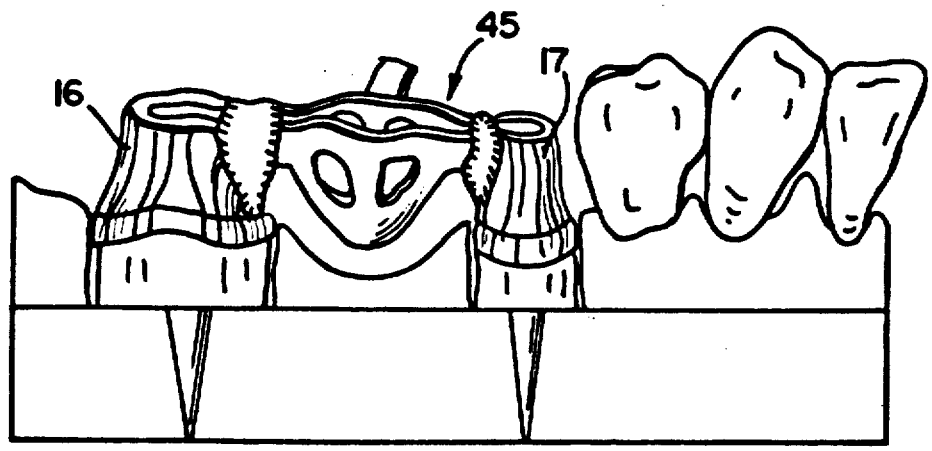
FIG. 7

METHOD FOR CONSTRUCTING A DENTAL BRIDGE USING A PREFABRICATED PONTIC

BACKGROUND OF THE INVENTION

1. Field of the Invention

The present invention is a continuation-in-part of U.S. patent application, Ser. No. 097,824, filed on Sept. 17, 1987, now U.S. Pat. No. 4,957,439, issued on Sept. 18, 1990 and entitled Prefabricated Dental Pontic, Pontic Connector and Assembly.

2. Description of the Prior Art

Crown and bridge prosthodontics is the science and art of the complete restoration of one or more teeth and the replacement of one or more natural teeth with an artificial device. A bridge is used to replace at least one missing tooth and is supported by natural teeth. A bridge which is not cast in one piece includes a pontic which fills the edentulous space and a connector which connects the pontic to a retaining member such as a crown formed on an abutment tooth adjacent the pontic. In the conventional bridge, the pontic is joined to the retainer solely by means of a solder joint which forms the connector.

The primary purpose of the dental bridge is to receive the forces of occlusion and to transmit them through the abutments so that occlusion is restored to the patient, thereby contributing to mastication. The bridge should also augment the ability of the patient to enunciate and maintain the positions of the opposing teeth. The present day construction of a dental bridge is a time consuming, involved and complex process which requires the application of many independent procedures including the following: waxing, spruing, investing, casting, cleaning, trimming, cutting and stoning. The process, as conventionally practiced, is referred to colloquially as the "lost wax casting method" and, at present, is the universally accepted procedure for making a bridge. Following this procedure is not only time-consuming, but each step must be meticulously followed with the dental technician paying strict attention to detail to assure accuracy of the cast product and proper fit. It is also difficult to make any adjustments to a cast bridge to compensate for errors.

Constructing a dental bridge from a prefabricated assembly including a pontic and retaining member(s) offers the advantage of speed, simplicity, and substantial cost savings over the cast bridge. However, conventional solder has proven to be too weak for use as the sole connector between the pontic and retaining member, particularly for posterior bridges.

SUMMARY OF THE INVENTION

The present invention permits a prefabricated pontic to be joined to a metal retainer using a technique which incorporates the use of conventional dental solder. The joint formed between the pontic and metal retainer using the method of the present invention is substantially superior in strength to that of a conventional solder joint, and equal to or greater in strength to the joint formed from casting a one-piece bridge.

The method of the present invention for constructing a dental bridge to one or more abutment teeth having a metal retaining member for each abutment tooth comprising the steps of:

mounting the metal retaining member(s) upon a die prepared from an impression of each abutment tooth or teeth;

positioning a metal pontic in the missing space adjacent the retaining member(s), with said pontic having a body and at least one solid arm extending from the body, with an open end approximate the retaining member;

securing the relative position between the pontic and each metal retaining member;

forming a dental material comprising a precious metal composition of high-fusing temperature metal particles and low-fusing temperature metal particles, with the high-fusing particles being substantially greater in size than the low-fusing metal particles, and in a relationship by volume such that upon heat treatment, a porous structure is formed having a void volume of between 20 to 80 percent;

applying said dental material to form an interproximal joint between the open end of the arm and the adjacent retaining member;

adding dental solder to said dental material;

heat treating said pontic and metal retaining member(s) at a temperature above the melting temperature of said low-fusing temperature metal particles, but below the melting temperature of said solder; and raising the heat treatment temperature to cause the solder to melt to form a solid joint at the interproximal.

BRIEF DESCRIPTION OF THE DRAWING

Comprehension of the invention is facilitated by reading the following detailed description of the invention in conjunction with the following drawing of which:

FIG. 1 is a side elevation of a model of a die of two prepared abutment teeth separated by an edentulous space representing a missing tooth or teeth;

FIG. 2 is a side elevation of the model of FIG. 1 with a prefabricated metal retaining member mounted on each abutment tooth;

FIG. 3 is a side elevation, similar to FIG. 2, with a prefabricated metal pontic shown positioned between each adjacent retaining member;

FIG. 4 is a side elevation of an investment model showing the metal pontic secured in the investment between the retaining members;

FIG. 5 is a side elevation of the model of FIG. 4, with dental material and solder applied to build up the area between the pontic arms and metal retainers;

FIG. 6 is a side elevation, similar to FIG. 5, showing the invested bridge components after heat treatment; and FIG. 7 shows the finished metal framework of the bridge in side elevation placed back on the die model of FIG. 1.

DETAILED DESCRIPTION OF THE INVENTION

FIG. 1 shows a conventional working model (10) with two removable stone dies (12) and (13) separated by a space (14), representing the missing tooth to be restored by the construction of a bridge. In FIG. 2, the two removable stone dies (12) and (13) are fitted with metal retainers (16) and (17), respectively. The metal retainers (16) and (17) protect the abutment teeth and serve as structural supports for the dental bridge. The abutment teeth of the patient may be prepared for a full crown, partial crown or metal inlay. In the construction of a crown, particularly a full crown, the metal retainer is referred to as a metal coping. The design of the metal retainer is not critical to the present invention, nor is the configuration or method of construction used in forming the metal retainer critical to the present invention. A preferred prefabricated metal retaining member for a full crown constructed from a relatively thin metal foil, without casting, is disclosed in U.S. Pat. Nos. 4,273,580, 4,459,112, and 4,492,579, respectively. The metal foil, as taught in the latter two patents, is preconfigured into a geometry with multiple folds which extend from a central area defining the occlusal surface of the coping. The metal retaining members (16) and (17) are representative of full crown metal copings which are adapted to the respective dies (12) and (13) of the abutment teeth using a conventional swaging device, as is well known to those skilled in the art.

The pontic of the present invention (20) is preferably a prefabricated metal structure, as shown in FIG. 3, having a geometry which may vary depending upon the restoration under construction. However, in each instance, the pontic (20) will comprise a metal body (22) having an arm (24) laterally extending from at least one end of its metal body (22). The pontic (20) may be composed of any suitable metal or metal alloy composition, the selection of which should meet the standards of compatibility for use in the oral cavity. Accordingly, the pontic should preferably include gold as at least one of its constituent elements. In addition, any conventional manufacturing method may be used to prefabricate the pontic (20), including conventional die casting and metal stamping.

The pontic body (22) may be shaped to form any desired configuration, preferably with open spaces (25). In fact, the geometrical shape of the pontic body (22) may vary considerably, based upon whether a molar or anterior restoration is involved. Although the geometry of the pontic body (22) is not critical to the present invention, a cradle-like geometry is preferred, particularly for a posterior restoration. The pontic should be constructed in accordance with the principles of construction taught and described in U.S. Pat. No. 4,231,740, the disclosure of which is herein incorporated by reference. The cradle-like geometry should have a large, occlusal concavity (26). The body (22) of the pontic (20) should have wings (27) and (28), which extend outwardly toward the buccal and lingual surfaces of the restoration. The open spaces (25) provide an open metal framework. The underside (29) of the body (22) may loop occluso-gingivally to form an arch.

The preferred metal body design for an anterior restoration is not shown, but is taught in general in U.S. Pat. No. 4,318,697, the disclosure of which is herein incorporated by reference. The primary difference in geometry between the posterior and anterior design is the addition of an occlusal brace which extends substantially upright, and a depending, blade-like extension which is directed gingivally.

The arms (24) of the pontic (20) are preferably symmetrical and of the same uniform dimension and thickness, although such symmetry and equivalent dimensional thickness is not necessary. In a three-unit bridge, two arms (24) are used to symmetrically support the pontic (20) between the two metal retainers (16) and (17), as shown in FIG. 3. Each arm (24) should be rigid, although its shape is not critical. Accordingly, the arms (24) may be solid or have a geometry with a cross-sectional trough-like channel (30). Alternatively, the cross-sectional geometry of each arm (24), as shown in FIG. 3, may be "U-shaped," "V-shaped" or box-shaped with an open top. The length of each arm (24) is not a critical dimension and may provide the pontic (20) with an overall length which is greater than the spacing between the metal retainers (16) and (17). In this instance, at least, one of the arms (24) should be shortened or cut to permit the pontic (20) to be loosely positioned between the metal retainers (16) and (17), as is shown in FIG. 3, such that a small distance or gap ("X") exists between the free end of each arm (24) and the adjacent metal retainers (16) and (17). The gap, "X," is not critical and typically 1 mm would suffice.

The pontic (20) is positioned and joined to the metal retainers (16) and (17) using wax and a supporting rod (not shown), as is well known to the dental technician or dentist. Alternatively, other conventional joining and alignment techniques may be used to secure the relative position of the pontic (20) to the retaining members. After the pontic (20) and the metal retainers (16) and (17) are secured in position, the bridge members are invested with conventional refractory investment material to form an investment or soldering model (32), as shown in FIG. 4. FIG. 4 shows the two abutment metal retainers (16) and (17) and the pontic (20) on the soldering model (32), with the investment material (34) holding the underside (29) of the pontic body (22) in a fixed position relative to the metal retainers (16) and (17), so that they may be soldered together in accordance with the present invention.

The solder operation of the present invention requires the use of a composition of metal particles (40) comprising particles of a high-fusing temperature metal which will melt substantially above 1200° C., preferably particles of precious metal such as palladium or platinum, or a combination thereof, and particles of a low-fusing temperature metal which will melt below 1200° C., and preferably between 1000° C. and 1100° C., such as, for example, using precious metal particles of gold or a gold alloy. The particles of high-fusing temperature metal are substantially larger, and preferably over five times larger, than the particles of low-fusing temperature metal, and preferably between five and ten times larger. The low-fusing component should be selected in a relationship by volume to said high-fusing component based on their relative specific gravities and proportion to one another, such that by heat treating the composition of particles at a temperature above the melting temperature of the low-fusing temperature metal particles, an open, porous sponge structure of metal is formed, having a total void volume of between twenty to eighty percent (20% to 80%), and preferably between forty to sixty percent (40% to 60%). The high- and low-fusing temperature components should be selected so that the high-fusing component is at least thirty percent (30%) by volume of the porous sponge structure, and preferably less than sixty percent (60%) by volume. This composition (40) of metal particles is more fully described in a corresponding patent application, U.S. Ser. No. 352,713, filed May 12, 1989, the disclosure of which is herein incorporated by reference.

The aforementioned dental composition (40) may be applied to the bridge structure, as shown in FIG. 5, by means of a brush or spatula, and may, if desired, be burnished or molded by hand into a desired shape to shape the interproximal points.

Particles of a conventional solder metal (42), such as dental gold alloy solder composition, is placed on top of the shaped dental composition (40), as shown in FIG. 6, before or after heat treatment. The melting temperature of the solder gold alloy should be slightly greater than the melting temperature of the low-fusing temperature metal component of the dental composition (40). By placing pieces of solder metal on the dental composition before heat treatment, only one heat treatment operation is necessary. The solder model and the bridge elements are then placed in a furnace for heat treatment. The temperature of the furnace is first raised to the melting temperature of the low-fusing temperature metal particles in the composition, which would be 1000° C. for gold particles. This causes the composition to sinter, as explained in corresponding U.S. patent application, Ser. No. 352,713, to form a porous sponge structure with a substantial void volume. The temperature is then further raised to the melting temperature of the dental solder, e.g., 1120° C., causing the solder metal to flow into the porous voids in the sponge, to create a solid joint which is substantially stronger than using solder alone. The investment is then removed, leaving a metal framework (45), as shown in FIG. 7.

The metal bridge frame (45) may be returned to the die model of FIG. 1, as shown in FIG. 7, for adding porcelain or another veneering material to finish the bridge. Alternatively, it may be used as a metal bridge without a covering. Tests were conducted to determine the strength of a dental bridge constructed in accordance with the present invention, and found to withstand pressures of at least 250 kg without breakage at the interproximal metal connections.

What we claim is:

1. A method of constructing a dental bridge to one or more abutment teeth having a metal retaining member for each abutment tooth, comprising the steps of:
    mounting the metal retaining member or members upon a die prepared from an impression of each abutment tooth or teeth;
    positioning a metal pontic in a missing space adjacent the retaining member or members, with said pontic having a body and at least one solid arm extending from the body, with an open end adjacent the retaining member;
    securing the relative position between the pontic and each metal retaining member;
    forming a dental material comprising a precious metal composition of high-fusing temperature metal particles and low-fusing temperature metal particles, with the high-fusing particles being substantially greater in size than the low-fusing metal particles, and in a relationship by volume such that upon heat treatment, a porous structure is formed having a void volume of between 20 to 80 percent;
    applying said dental material to form an interproximal joint between the open end of the arm and the adjacent retaining member;
    adding dental solder to said dental material;
    heat treating said pontic and metal retaining member or members at a temperature above the melting temperature of said low-fusing temperature metal particles, but below the melting temperature of said solder; and
    raising the heat treatment temperature to cause the solder to melt to form a solid joint at the interproximal joint.

2. A method, as defined in claim 1, wherein the open end of each arm of said pontic forms a gap separating the open end from the adjacent retaining member.

3. A method, as defined in claim 2, wherein the dental material applied to form the interproximal joint is shaped into a desired shape prior to said heat treatment.

4. A method, as defined in claim 3, wherein said high-fusing temperature metal particles comprise precious metal particles selected from the group consisting of palladium and platinum.

5. A method, as defined in claim 4, wherein said low-fusing temperature metal particles comprise precious metal particles of gold or a gold alloy.

6. A method, as defined in claim 5, wherein the high-fusing and low-fusing particles are selected so that the high-fusing component are between 30 and 60 percent by volume of the porous structure.

7. A method, as defined in claim 6, wherein said pontic has a geometry with open spaces.

* * * * *